(12) United States Patent
Stylos (10) Patent No.: US 8,700,143 B2
(45) Date of Patent: Apr. 15, 2014

(54) ADAPTATIONS TO OPTIVOL ALERT ALGORITHM

(75) Inventor: Lee Stylos, Stillwater, MN (US)

(73) Assignee: Medtronic, Inc., Minneapolis, MN (US)

( * ) Notice: Subject to any disclaimer, the term of this patent is extended or adjusted under 35 U.S.C. 154(b) by 1617 days.

(21) Appl. No.: 11/567,835

(22) Filed: Dec. 7, 2006

(65) Prior Publication Data
US 2008/0024293 A1    Jan. 31, 2008

Related U.S. Application Data

(63) Continuation-in-part of application No. 11/460,703, filed on Jul. 28, 2006, now Pat. No. 8,055,335.

(51) Int. Cl.
*A61B 5/05* (2006.01)

(52) U.S. Cl.
USPC .......................................................... 600/547

(58) Field of Classification Search
USPC ................. 600/547, 300, 485, 506, 508, 510; 607/6, 17
See application file for complete search history.

(56) References Cited

U.S. PATENT DOCUMENTS

| 5,876,353 | A  | 3/1999  | Riff |
| 5,957,861 | A  | 9/1999  | Combs et al. |
| 6,512,949 | B1 | 1/2003  | Combs et al. |
| 6,829,503 | B2 | 12/2004 | Alt |
| 6,931,272 | B2 | 8/2005  | Burnes |
| 2002/0147475 | A1 | 10/2002 | Scheiner et al. |
| 2003/0023184 | A1 | 1/2003  | Pitts-Crick et al. |
| 2003/0028221 | A1 | 2/2003  | Zhu et al. |
| 2004/0102712 | A1 | 5/2004  | Belalcazar et al. |
| 2004/0172080 | A1 | 9/2004  | Stadler et al. |
| 2005/0124908 | A1 | 6/2005  | Belalcazar et al. |
| 2005/0137480 | A1 | 6/2005  | Alt et al. |
| 2006/0020295 | A1 | 1/2006  | Brockway et al. |

FOREIGN PATENT DOCUMENTS

WO      2004050178      6/2004

OTHER PUBLICATIONS

Pandey et al, Tracking Based Baseline Restoration for Acquisition of Impedance Cardiogram and Other Biosignals, Proceedings of the 2005 IEEE Engineering in Medicine and Biology 27th Annual Conference, Shanghai, China, Sep. 1-4, 2005, pp. 3486-3489.*
International Search Report, PCT/US2007/072196, Feb. 21, 2008, 2 Pages.
International Search Report, PCT/US2007/086721, Jun. 19, 2008, 3 Pages.

* cited by examiner

*Primary Examiner* — Brian Szmal
(74) *Attorney, Agent, or Firm* — Reed A. Duthler; Stephen W. Bauer (57) ABSTRACT

Adaptations to the OptiVol™ alert algorithm are disclosed which may reduce the number of false positive alerts while retaining the desired sensitivity. Some embodiments monitor fluid levels in patients. Some embodiments reset a cumulative index when a short-term impedance value is greater than a baseline impedance value minus a predetermined positive hysteresis value.

17 Claims, 5 Drawing Sheets

$$Z_m = \frac{V_m}{V_o/V_o}$$

ADAPTATIONS TO OPTIVOL ALERT ALGORITHM

RELATED APPLICATIONS

This application is a continuation-in-part application of prior patent application Ser. No. 11/460,703 filed Jul. 28, 2006 now U.S. Pat. No. 8,055,335, entitled "Adaptations to Intra-Thoracic Fluid Monitoring Algorithm".

BACKGROUND

Some embodiments disclosed herein relate generally to enhancing therapy. Impedance monitoring is often used with implantable medical devices and in external monitoring devices for determination of numerous physiologic conditions. Transthoracic impedance measurements can give a good indication of the fluid status of patients, with decreases in impedance being indicative of increases in fluid content and increases in impedance being indicative of decreases in fluid content. Knowledge of a patient's long-term impedance measurements and changes therein are a valuable clinical indicator of a patient's health.

The accumulation of fluid can indicate failing heart circulation as well as several other conditions. There are several mechanisms or diseases that can cause or affect the accumulation of fluid. In general, fluid accumulation is a failure or over-response of the homeostatic process within the body. The body normally prevents the build up of fluids by maintaining adequate pressures and concentrations of salt and proteins and by actively removing excess fluid. Fluid accumulation can occur, for example, when the body's mechanisms for preventing fluid accumulation are affected by disease, such as heart failure, left-sided myocardial infarction, high blood pressure, altitude sickness, emphysema (all of which affect pressures), cancers that affect the lymphatic system, renal diseases, and diseases that disrupt the protein concentrations. Likewise, abnormally low fluid levels can also be problematic. As a result, providing an adequate monitor of the patient's fluid status can provide physicians and patients with a better tool to manage disease.

Upon detection of predetermined impedance values indicating abnormal fluid status, the patient can be notified to seek professional care. In this way, a clinician is able to address the patient's fluid status, which may be the result of cardiac decompensation during heart failure, earlier. This allows patients to receive professional care (e.g., medications like diuretics and beta blockers in heart failure patients) much sooner, thereby decreasing the likelihood of the fluid status developing into a more serious condition.

Determining the impedance values at which to notify a patient can prove difficult. On one hand, patients should be notified every time they are approaching a dangerously high or low fluid status. On the other hand, notifying patients when they face no dangerously high or low fluid status can result in the unnecessary consumption of time and resources. This can be especially problematic when the unnecessary consumption is multiplied over a large patient population.

DETAILED DESCRIPTION OF ILLUSTRATIVE EMBODIMENTS

The following detailed description of illustrative embodiments should be read with reference to the drawings, in which like elements in different drawings are numbered identically. The drawings depict illustrative embodiments and are not intended to limit the scope of the invention. Rather, the present invention is defined solely by the claims.

Figure 1:
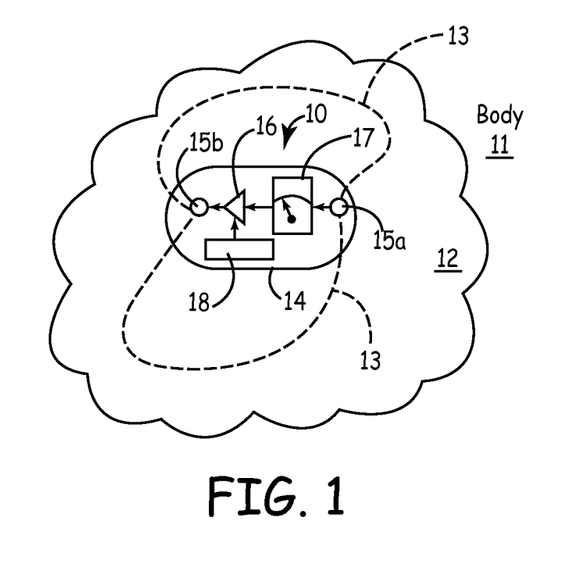
FIG. 1 is a schematic diagram of an implantable medical device.

FIG. 1 is a schematic diagram of an exemplary implantable medical device 10 according to an embodiment of the present invention. A section of a body 11 is shown with a cut-away area 12 to allow for illustration of an implantable medical device 10. The implantable medical device 10 includes two electrodes 15a and 15b on the surface of a shell 14 of device 10. Power is provided to the circuitry internal to the shell 14 by a power supply 18, which drives a stimulation circuit 16, sending electrons through various pathways in the body between electrodes 15a and 15b. The pathways are illustrated as being primarily in the area surrounded by dotted line 13. An impedance measurement device 17 determines the impedance of the circuit pathway 13.

Figure 2:
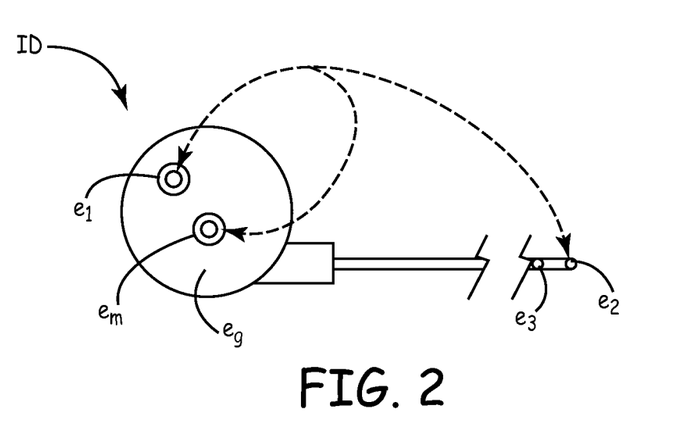
FIG. 2 is a schematic diagram of exemplary electrode configurations in an implantable medical device.

FIG. 2 is a schematic diagram of exemplary electrode configurations in an implantable medical device. The different configurations can achieve different impedance measurement signal values. For example, the implantable medical device has electrodes (e1), (e2), (eg), and (em). Electrode (e1) or electrode (e2) can be used for developing the test pulses. The value being measured (voltage or impedance of the tissue between these electrode pairs) is taken between one of three electrode pairs: (1) an electrically isolated measuring electrode (em) and the indifferent or ground electrode (eg), (2) electrode (em) and electrode (e1), or (3) electrode (em) and electrode (e2). Or, of course, the measurement could be taken between the two test pulse delivery electrodes (e1) and (eg), or between electrode (e2) and electrode (eg).

Figure 3:
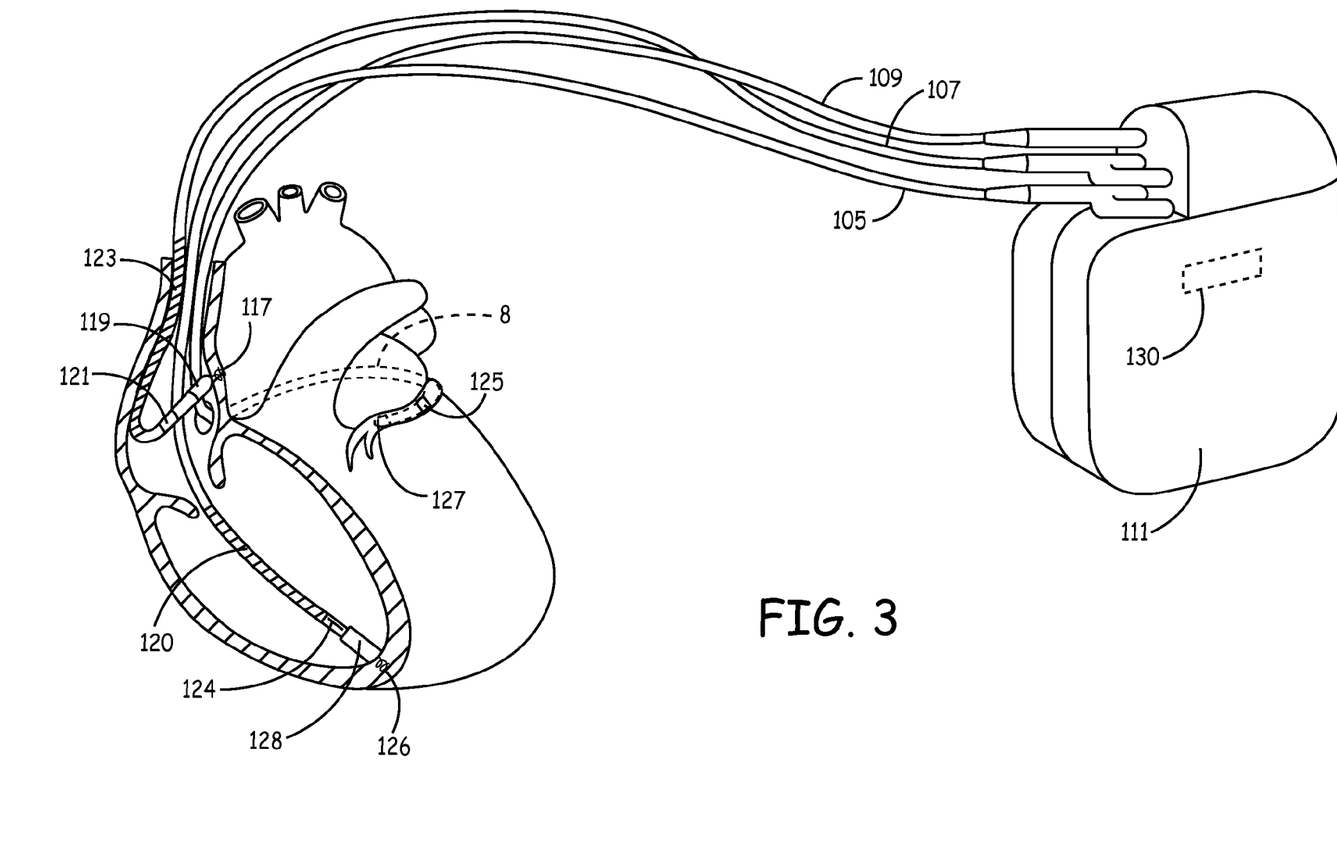
FIG. 3 is a schematic diagram of an implantable medical device in which the present invention may usefully be practiced.

FIG. 3 is a schematic diagram of an exemplary implantable medical device in which the present invention may usefully be practiced. The implantable medical device includes a hermetically sealed enclosure 111 and three leads: a ventricular lead 105, an atrial/SVC lead 107, and a coronary sinus/coronary vein lead 109. The enclosure 111 contains the electronic circuitry used for generating cardiac pacing pulses for delivering cardioversion and defibrillation shocks and for monitoring the patient's heart rhythm. Examples of such circuitry are well known in the art. The ventricular lead 105 carries three electrodes adjacent its distal end: a ring electrode 124, an extendable helix electrode 126 mounted retractably within an insulative electrode head 128, and an elongated coil electrode 120. The atrial/SVC lead 107 carries the same three electrodes adjacent its distal end: a ring electrode 121, an extendible helix electrode 117 mounted retractably within an insulative electrode head 119, and an elongated coil electrode 123. The coronary sinus/coronary vein lead 109 carries an electrode 108 (illustrated in broken outline) that is located within the coronary sinus and great vein of the heart. The coronary sinus/coronary vein lead 109 also carries a ring electrode 125 and a tip electrode 127 adjacent its distal end.

Figure 4:
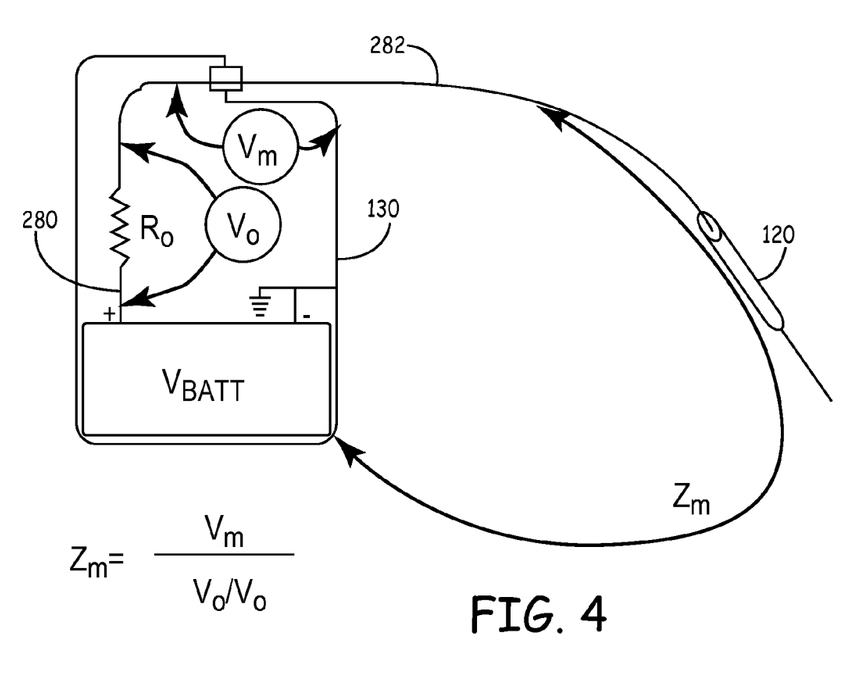
FIG. 4 is a schematic diagram illustrating an exemplary method of measuring impedance.

FIG. 4 is a schematic diagram illustrating an exemplary method of measuring impedance according to an embodiment of the present invention. To generate a transthoracic impedance $Z_m$ measurement, a pacer timing and control circuit initiates, via control circuitry, delivery of a predetermined voltage pulse $V_o$ from an output circuit along an excitation path 280 between electrodes 120 and 130. A resistor $R_o$ having a known resistance is incorporated in the output circuit, positioned along the excitation path 280 so that the current $I_o$ delivered along the excitation path 280 can be calculated, using Ohm's Law, as $I_o = V_o/R_o$. The voltage $V_m$ is measured across the measurement path 282 between a point after resistor $R_o$ and electrode 130, and, knowing the current $I_o$ delivered to the measurement path 282, impedance $Z_m$ is calculated as $Z_m = V_m/(V_o/R_o)$.

According to certain embodiments of the present invention, raw impedance measurements are collected a predetermined number of times per day (e.g., one measurement every 20 minutes) during one or more predetermined periods of the day (e.g., between noon and 5 pm). A daily mean impedance is determined by averaging the raw impedance measurements. An expected, or baseline (BL), impedance is computed by taking a very low pass filtered version of the daily mean impedance. The BL impedance is intended to represent the patient's normal long-term impedance (e.g., when excessive fluid is not present). The value of a BL impedance varies from patient to patient and according to the chosen measurement vector. For instance, when the medical device is used as one of the electrodes (as in the embodiment of FIG. 4), the BL impedance can be between approximately 50 ohms and 90 ohms. A short term average (STA) impedance is computed by taking a slightly filtered version of the daily mean impedance. The STA impedance is intended to be a best estimate of the current impedance.

These measurements may, for example, be obtained from pre-programmed vectors chosen for the excitation path and the measurement path, such as the ring (e3) to case (eg) and tip (e2) to case (eg) arrangement of FIG. 2. Referring to FIG. 3, the RV coil electrode 120 and housing electrode 130 may, for example, be utilized for both the excitation path and the measurement path. However, it is understood that other arrangements can also be utilized, such as an arrangement in which the excitation path is between electrode 123 and electrode 130 and the measurement path is between electrode 117 and electrode 130. Another operative vector could be an RV coil 120 to the enclosure 111 vector with a left pectoral implant. Another could be a vector from an SVC coil 123 to an RV coil 120. However, most any vector for impedance monitoring could be used. It is further contemplated that the leads can be epicardial leads and/or subcutaneous leads. Enclosure 111 can be implanted in a sub-muscular or subcutaneous location anywhere about the chest. In some embodiments, the enclosure 111 is located in a region other than the pectoral region.

Once an initial stabilization time period has expired after implantation (e.g., 45 days for implantation of larger medical devices), initial values of the BL impedance and the STA impedance are established. Observing a stabilization period avoids inaccurate (e.g., artificially low) impedance readings caused by fluid buildup in the thoracic cavity stemming from the recovery from implantation of device. Once the BL impedance and the STA impedance are established, changes in the daily mean impedance values over time are monitored for indications of abnormal fluid status. Monitoring impedance data is discussed in the following paragraphs and in U.S. patent application Publication No. 2004/0172080 to Stadler et al., titled "Method and Apparatus for Detecting Change in Intrathoracic Electrical Impedance," which is incorporated by reference herein in relevant part.

Figure 5:
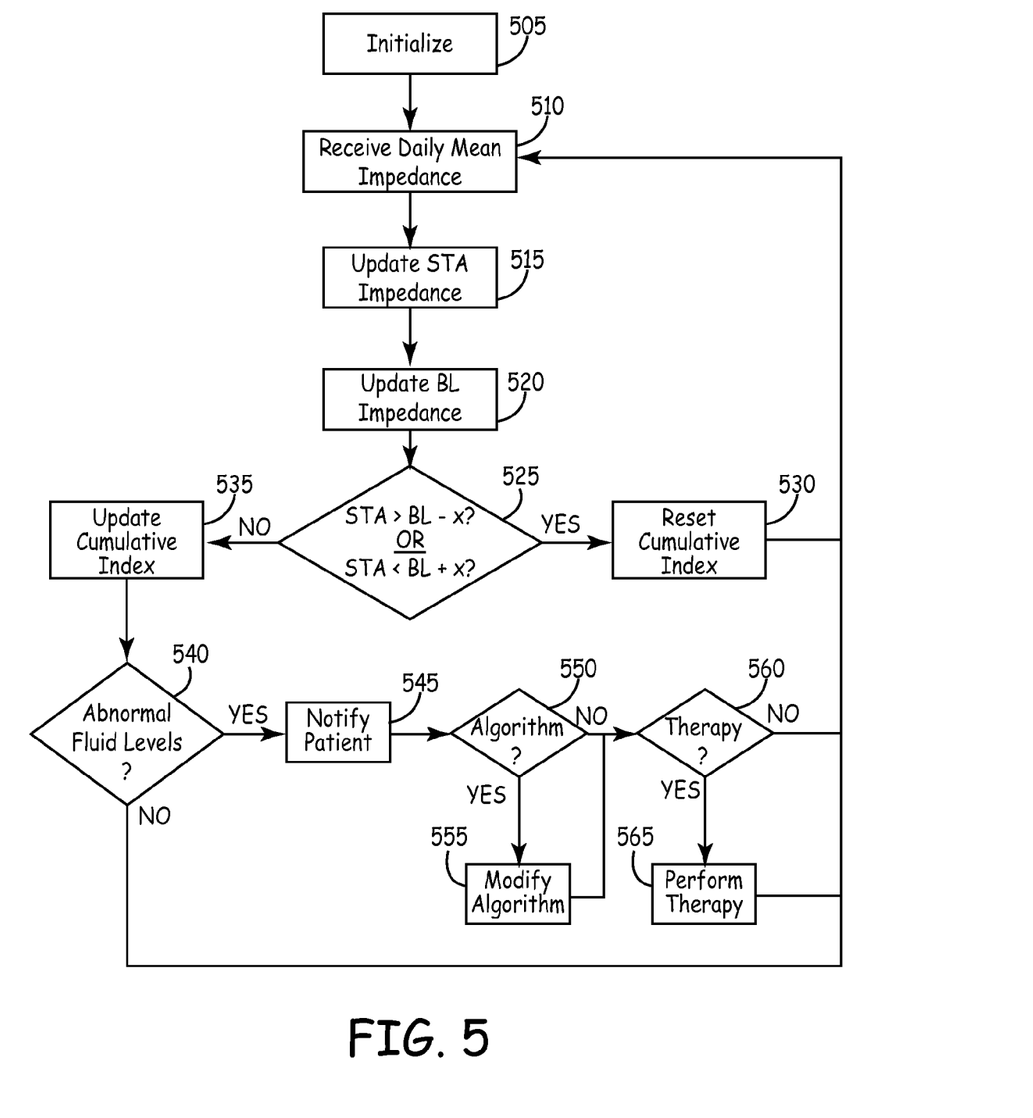
FIG. 5 is a flow chart illustrating an exemplary method by which a system can monitor impedance data.

FIG. 5 is a flow chart that shows an exemplary method by which a system can monitor impedance data according to the present invention. The system first establishes the initial values of the BL impedance and the STA impedance (505), as set forth above. Then the system receives a daily mean impedance (510) and updates the STA impedance and the BL impedance (515), (520) based on that daily mean impedance. In some embodiments, the STA impedance is updated (515) by taking a weighted sum of (a) the STA impedance for the two previous days and (b) the daily mean impedance for the current day and the two previous days. In such embodiments, the STA impedance can be relatively responsive to changes in the daily mean impedance. In many embodiments, the BL impedance is updated (520) at a much slower rate than the STA impedance. The BL impedance is updated (525) based on the STA impedance. That is, if the newly-calculated STA impedance is less than the BL impedance, the BL impedance is adjusted downward by a predetermined downdrift (e.g., 0.055 ohms per day), and if the newly-calculated STA impedance is greater than the BL impedance, the BL impedance is adjusted upward by a predetermined updrift (e.g., 0.18 ohms per day).

After updating the STA impedance and BL impedance (515),(520), the system can determine whether the impedance data indicates normal or abnormal fluid levels. This method is especially applicable when the STA impedance measures consistently and significantly below the BL impedance— a trend that could indicate abnormally high fluid levels. Accordingly, when a given STA impedance is either greater than the corresponding BL impedance or within a predetermined hysteresis (X) of the corresponding BL impedance, it can be inferred that this trend is not present and that fluid levels are normal. Likewise, this method can be especially applicable when the STA impedance measures consistently and significantly above the BL impedance— a trend that could indicate abnormally low fluid levels. In such a situation, when a given STA impedance is either less than the corresponding BL impedance or within a predetermined hysteresis (X) of the BL impedance, it can be inferred that this trend is not present and that fluid levels are normal.

With this in mind, after updating the STA impedance and the BL impedance (515), (520), the system can compare the newly-calculated STA impedance value with the newly-calculated BL impedance value, in light of the predetermined hysteresis value, to determine whether the monitored trend is absent (525). In embodiments in which a patient is being monitored for abnormally high fluid levels, this comparison can involve determining whether the newly-calculated STA impedance is greater than the newly-calculated BL impedance less the predetermined hysteresis value (X). In embodiments in which a patient is being monitored for abnormally low fluid levels, this comparison can involve determining whether the newly-calculated STA impedance is less than the sum of the corresponding BL impedance and the predetermined hysteresis value (X). If the system determines that the monitored trend is absent, the system can reset the cumulative index (530). Stated another way, in response to the result of the comparison indicating that the STA impedance is either greater than the corresponding BL impedance or within a predetermined hysteresis (X) of the corresponding BL impedance, it can be inferred that the fluid levels are normal as stated in paragraph 21 above. In other words, the short-term representative value indicates normal fluid levels in response to the short-term representative value being greater than the long-term representative value plus or minus the first predetermined hysteresis value. Similarly, the result of the comparison will indicate that the fluid levels are normal in response to the STA impedance being either less than the corresponding BL impedance or within a predetermined hysteresis (X) of the BL impedance as stated in paragraph 21 above. In other words, the short-term representative value indicates normal fluid levels in response to the short-term representative value being less than the long-term representative value plus or minus the second predetermined hysteresis value. In some instances, a clinician can initiate the reset (full or soft) manually. In such embodiments, the manual reset can be performed via telemetry, via a pushbutton on the enclosure, or via other suitable means. After resetting the cumulative index (530), the system can wait to receive the next daily mean impedance (510), at which time the process can be repeated. If the system cannot determine that the trend is absent, the system updates the cumulative index (535). In embodiments in which a patient is being monitored for abnormally high fluid levels, the cumulative index can comprise previous days' BL impedances minus corresponding STA impedances. In embodiments in which a patient is being monitored for abnormally low fluid levels, the cumulative index can comprise previous days' STA impedances minus corresponding BL impedances.

After updating the cumulative index (535), the system can determine whether the updated cumulative index indicates abnormal fluid levels (540). In some embodiments, the system makes this determination by comparing the cumulative index to a predetermined threshold, which is established by a clinician according to factors that are discussed in more detail below. If the system determines that the cumulative index does not indicate abnormal fluid levels, the system can wait to receive the next daily mean impedance (510), at which time the process can be repeated. On the other hand, if the system determines that the cumulative index does indicate abnormal fluid levels, the system can notify the patient (545) (e.g., by an audible alarm, by vibration, by stimulation, by communication to an external device, etc.).

In addition, in some embodiments, the system can modify the algorithm for detecting changes in impedance in response to the detection of abnormal fluid levels. For example, the interval at which the daily mean impedance is calculated could be increased (e.g., from once per day to once per hour). In such embodiments, the system first determines whether to modify the algorithm (550). If the system determines that it should not modify the algorithm, the system can move on to the next step. If the system determines that it should modify the algorithm, the system does so (555) and then moves on to the next step. In some embodiments, the system can initiate or modify therapy when an abnormal fluid level is detected. In such embodiments, the system first determines whether to initiate or modify therapy (560). If the system determines that it should not initiate or modify therapy, the system can wait to receive the next daily mean impedance (510) (while the patient hopefully seeks professional care), at which time the process can be repeated. If, on the other hand, the system determines that it should initiate or modify therapy, the system does so (565). Examples of such therapy include activating a drug pump, a pacing mode, or a pacing rate, or performing cardiac resynchronization therapy (CRT) or cardiac potentiation therapy (CPT). After initiating or modifying therapy, the system can wait to receive the next daily mean impedance (510) (while the patient hopefully seeks professional care), at which time the process can be repeated.

The order of steps provided in the methods shown in FIG. 5 is provided for purposes of illustration only, and other orders that achieve the functionality recited are within the scope of the present invention. Any of the functionality discussed anywhere in this disclosure may be implemented in the method shown in FIG. 5.

Figure 6:
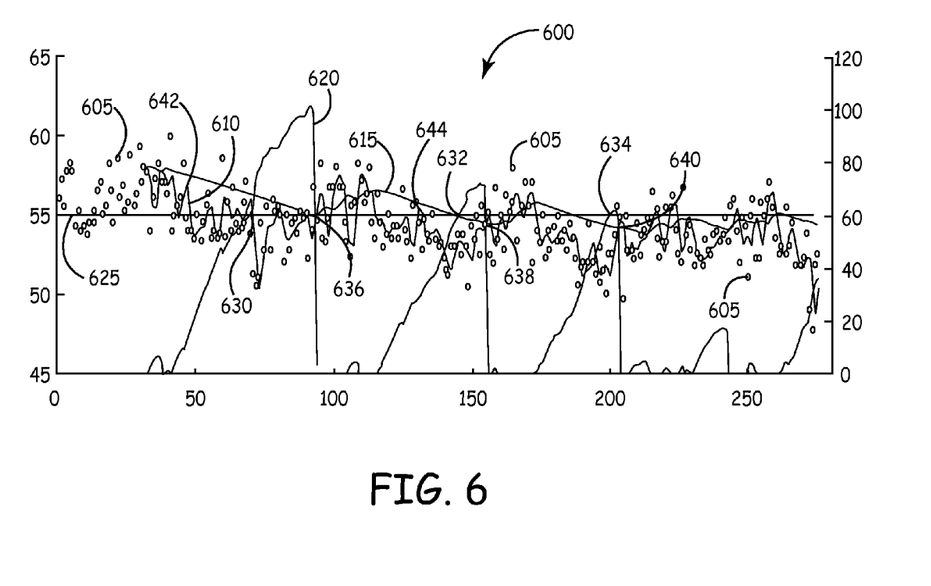
FIG. 6 is a plot of exemplary impedance measurements taken pursuant to an embodiment of the method of FIG. 5.

FIG. 6 shows a plot 600 of exemplary impedance measurements taken pursuant to an embodiment of the method of FIG. 5. Referring to FIG. 6, the plot 600 has time (measured in days) as its X-axis, impedance (measured in ohms) as its left Y-axis, and impedance-time (measured in ohm-days) as its right Y-axis. Values represented on the plot 600 include daily mean impedance values 605, STA impedance values 610, BL impedance values 615, the cumulative index 620, and the predetermined threshold 625. The daily mean impedance values 605, STA impedance values 610, and BL impedance values 615 are tied to the left Y-axis, and the cumulative index 620 and the predetermined threshold 625 are tied to the right Y-axis. As discussed above, each daily mean impedance value 605 impacts that day's STA impedance value 610 and BL impedance value 615, with the STA impedance values 610 being more responsive to changing daily mean impedance values 605. As also discussed above, the cumulative index 620 is impacted by the difference between the BL impedance values 615 and the STA impedance values 610. Specifically, the embodiment of FIG. 6 involves a patient being monitored for abnormally high fluid levels. In this embodiment, that difference for a given day is added to that difference from previous days, unless that day's STA impedance value 610 is greater than that day's BL impedance value 615 less a predetermined hysteresis value, in which case the cumulative index 620 is reset. Once the cumulative index 620 reaches the predetermined threshold 625, the patient is notified, therapy is initiated or modified, and/or the algorithm is modified, as discussed above. As can be seen from the plot 600, the patient is notified on Day 630, Day 632, and Day 634.

In the system of plot 600, the predetermined hysteresis is set at zero ohms. As a result, a day's STA impedance value 610 must exceed the corresponding BL impedance value 615 to reset the cumulative index 620. This occurs on Day 636, Day 638, and Day 640, among others.

While systems that reset the cumulative index when a day's STA impedance value 610 exceeds the day's BL impedance value 615 are remarkably successful in detecting abnormally high levels, they can sometime result in an inordinately high number of false positives. When a patient is notified of a possible abnormal fluid level, he or she typically seeks professional care relatively quickly. A clinician then determines whether the patient does, in fact, have an abnormal fluid level. If the patient has an abnormal fluid level, he or she receives treatment to restore proper fluid levels (e.g., intravenous diuretics). If the patient does not have an abnormal fluid level (i.e., the abnormal fluid level notification was a false positive), he or she may leave the professional care facility without receiving any treatment. Such false positives consume valuable time and resources, both of the clinician and of the patient.

One way to reduce the number of false positives is to alter the predetermined threshold 625. For instance, in monitoring for abnormally high fluid levels, if the cumulative index 620 must reach a higher value before notifying the patient, there will likely be fewer of such notifications. For example, if the predetermined threshold 625 were set to 80 ohm-days rather than 60 ohm-days, neither Day 632 nor Day 634 would result in patient notifications. The downside of increasing the predetermined threshold 625 is decreased sensitivity. In other words, the system may fail to notify the patient when the patient is actually experiencing abnormal fluid levels.

One way to reduce the number of false positives while retaining the desired sensitivity is to increase the predetermined hysteresis value to a value greater than zero ohms. In other words, in such systems, the cumulative index 620 is reset, not when the STA impedance value 610 exceeds the BL impedance value 615, but when the STA impedance value 610 comes within the hysteresis value of the BL impedance value 615. For example, the patient represented in plot 600 was notified falsely of abnormally high fluid levels three times (on Day 630, Day 632, and Day 634); he or she never had abnormally high fluid levels. Increasing the hysteresis value would have resulted in the cumulative index 620 being reset on days in which the STA impedance value 610 was close to as high as the BL impedance value 615 (e.g., on Day 642 or Day 644). In many instances, resetting the cumulative index 620 on such days would prevent the patient from unnecessarily seeking professional care, thereby saving time and resources. In plot 600, if the cumulative index 620 were reset on Day 642 and Day 644, the patient would not likely have been falsely notified on Day 630 or Day 632.

A clinician can determine the appropriate hysteresis value based on a variety of factors. For example, in some instances, the size of the implantable medical device that houses the system can impact the hysteresis value. After all, in many embodiments, the implantable medical device acts as one of the poles of the impedance measurement (see FIG. 4). A larger implantable medical device often results in larger initial impedance values, and a smaller implantable medical device often results in smaller initial impedance values. Accordingly, a larger hysteresis value should be used with a larger implantable medical device, and a smaller hysteresis value should be used with a smaller implantable medical device. In other words, the hysteresis value can be a percentage of the initial impedance values. Likewise, in some instances, the nature of the patient can impact the hysteresis value. For some patients, the daily mean impedance values 605 vary widely from one day to the next, whereas for others, the daily mean impedance values 605 vary only minimally. A clinician can determine the patient's variability level by reviewing the patient's impedance values taken during the initialization phase. A larger hysteresis value should be used for patients whose daily mean impedance values 605 vary widely, and a smaller hysteresis value should be used for patients whose daily mean impedance values 605 vary only minimally.

The technique of adding a hysteresis value to an algorithm has been discussed in the context of thoracic impedance measurement. This technique, however, could be applied to systems monitoring fluid levels by measuring many types of physiological parameters (e.g., pressure, heart rate, respiration, etc.). For instance, in systems measuring pressure, abnormal fluid accumulation may result in the short-term pressure value being larger than the long-term pressure value, while abnormal fluid depletion may result in the short-term pressure value being smaller than the long-term pressure value. Moreover, this technique could be applied to systems monitoring fluid levels by measuring impedances in other parts of the body.

Certain embodiments may have one or more of the following advantages. In some embodiments, the number of false positives is decreased. In some embodiments, the sensitivity for notifying patients in "true positive" situations is retained. In some embodiments, the number of false positives can be decreased without adjusting the predetermined threshold. Some embodiments are adjustable for different kinds of implantable medical devices. Some embodiments are adjustable for different kinds of patients. Some embodiments are able to make use of impedance data gathered during the system's initialization period.

Some of the techniques described herein may be embodied as a computer-readable medium comprising instructions for a programmable processor. The programmable processor may include one or more individual processors, which may act independently or in concert. A "computer-readable medium" includes but is not limited to any type of computer memory such as floppy disks, conventional hard disks, CR-ROMS, Flash ROMS, nonvolatile ROMS, RAM and a magnetic or optical storage medium. The medium may include instructions for causing a processor to perform any of the features described above.

Thus, embodiments of the present invention are disclosed. One skilled in the art will appreciate that the present invention can be practiced with embodiments other than those disclosed. The disclosed embodiments are presented for purposes of illustration and not limitation, and the present invention is limited only by the claims that follow.

The invention claimed is:

1. A method of monitoring for abnormally high fluid levels by an implantable medical device, comprising:
the device intermittently measuring a physiological parameter value related to a patient's fluid level;
the device calculating a short-term representative value and an associated long-term representative value of the measured physiological parameter values after receipt of one or more of the measured physiological parameter values;
the device comparing each short-term representative value and the associated long-term representative value to determine if the short-term representative value indicates abnormal fluid levels, wherein abnormally high fluid levels are indicated responsive to the short-term representative value not being greater than the long-term representative value minus a first predetermined hysteresis value and abnormally low fluid levels indicated responsive to the short-term representative value not being less than the long-term representative value plus a second predetermined hysteresis value;
the device cumulatively adding a difference between the short-term representative value and the associated long-term representative value responsive to the short-term representative value not indicating normal fluid levels;
the device resetting the cumulative sum responsive to the short-term representative value indicating normal fluid levels; and
the device generating a notification in response to the cumulative sum exceeding a predetermined threshold value.

2. The method of claim 1, wherein the short-term representative value indicates normal fluid levels only responsive to the short-term representative value being greater than the long-term representative value minus the first predetermined hysteresis value and the short-term representative value is less than the long-term representative value plus the second predetermined hysteresis value.

3. The method of claim 1, wherein the short-term representative value comprises a short-term average value and the long-term representative value comprises a long-term average value.

4. The method of claim 1, wherein the second or first predetermined hysteresis value is based on a physical characteristic of the implantable medical device.

5. The method of claim 4, wherein the physical characteristic includes the size of the implantable medical device.

6. The method of claim 1, wherein the measured physiological parameter values comprise measured impedance values.

7. The method of claim 6, wherein the measured impedance values comprise measured transthoracic impedance values.

8. The method of claim 1, further comprising initiating therapy to the patient or modifying therapy being provided to the patient responsive to the cumulative sum exceeding the predetermined threshold value.

9. The method of claim 1, wherein notifying the patient of possible abnormal fluid levels includes one or more of (a) sounding an audible alarm, (b) vibrating, (c) causing stimulation, and (d) communicating to an external medical device.

10. An implantable medical device, comprising:
    a hermetically-sealed enclosure carrying an enclosure electrode;
    a lead including an electrode and having a proximal end and a distal end, the proximal end being functionally coupled to the enclosure; and
    circuitry housed within the enclosure, the circuitry being configured to:
        intermittently receive a measured physiological parameter value related to a patient's fluid level, the physiological parameter value being taken from the patient via the enclosure electrode and the lead electrode;
        calculate a short-term representative value and an associated long-term representative value of the measured physiological parameter values after receipt of one or more of the measured physiological parameter values;
        compare each short-term representative value and the associated long-term representative value to determine if the short-term representative value indicates normal fluid levels, the short-term representative value indicating abnormal fluid levels, wherein abnormally high fluid levels are indicated responsive to the short-term representative value not being greater than the long-term representative value minus a first predetermined hysteresis value and abnormally low fluid levels are indicated responsive to the short-term representative value not being less than the long-term representative value plus a second predetermined hysteresis value;
        cumulatively sum a difference between the long-term representative value and the short-term representative value responsive to the short-term representative value not indicating normal fluid levels; and
        reset the cumulative sum responsive to the short-term representative value indicating normal fluid levels.

11. The implantable medical device of claim 10, wherein the enclosure has a size, and the first or second predetermined hysteresis value is based on the size of the enclosure.

12. The implantable medical device of claim 10, wherein the short-term representative value indicates normal fluid levels only responsive to the short-term representative value being greater than the long-term representative value minus the first predetermined hysteresis value and the short-term representative value is less than the long-term representative value plus the second predetermined hysteresis value.

13. The implantable medical device of claim 10, wherein the intermittently received measured physiological parameter values have a degree of variation from day to day, and wherein the first or second predetermined hysteresis value is based on the degree of variation.

14. The implantable medical device of claim 10, wherein the intermittently received measured physiological parameter values comprise transthoracic impedance values.

15. A method of monitoring for abnormally high fluid levels by an implantable medical device, comprising:
    the device intermittently measuring a transthoracic impedance value;
    the device calculating a short-term representative value and an associated long-term representative value of the measured transthoracic impedance values after receipt of one or more of the measured transthoracic impedance values;
    the device comparing each short-term representative value and the associated long-term representative value to determine if the short-term representative value indicates normal fluid levels, the short-term representative value indicating normal fluid levels responsive to the short-term representative value being greater than the long-term representative value minus a high-fluid predetermined hysteresis value and the short-term representative value being less than the long-term representative value plus the second predetermined hysteresis value;
    the device cumulatively adding a difference between the long-term representative value and the short-term representative value responsive to the short-term representative value not being indicative of normal fluid levels;
    the device resetting the cumulative sum responsive to the short-term representative value indicating normal fluid levels; and
    the device generating a notification in response to the cumulative sum exceeding a predetermined threshold value.

16. The method of claim 15, notifying the patient of possible abnormal fluid levels includes one or more of (a) sounding an audible alarm, (b) vibrating, (c) causing stimulation, and (d) communicating to an external medical device.

17. The method of claim 15, further comprising initiating therapy to the patient or modifying therapy being provided to the patient responsive to the cumulative sum exceeding the predetermined threshold value.

* * * * *